(12) United States Patent
Saadat

(10) Patent No.: US 10,912,459 B1
(45) Date of Patent: Feb. 9, 2021

(54) SYSTEM AND METHOD FOR DETECTION OF OCULAR STRUCTURES

(71) Applicant: Neekon Saadat, Atherton, CA (US)

(72) Inventor: Neekon Saadat, Atherton, CA (US)

( * ) Notice: Subject to any disclaimer, the term of this patent is extended or adjusted under 35 U.S.C. 154(b) by 0 days.

(21) Appl. No.: 16/870,849

(22) Filed: May 8, 2020

(51) Int. Cl.
*A61B 3/14* (2006.01)
*A61B 3/12* (2006.01)
*A61B 3/00* (2006.01)
*C12Q 1/68* (2018.01)

(52) U.S. Cl.
CPC .......... *A61B 3/1216* (2013.01); *A61B 3/0008* (2013.01); *C12Q 1/68* (2013.01)

(58) Field of Classification Search
CPC ..... A61B 1/00039; A61B 3/14; A61B 3/0008; A61B 3/1173; A61B 3/18; A61B 3/12; A61B 3/1216; A61B 2090/309; A61B 2090/3612; A61B 2090/373
USPC .................................................. 351/206, 221
See application file for complete search history.

(56) References Cited

U.S. PATENT DOCUMENTS

| 9,642,517 | B2 * | 5/2017 | Wood | A61B 5/0077 |
| 2018/0365490 | A1 * | 12/2018 | Agrawal | G06K 9/0061 |
| 2019/0142269 | A1 * | 5/2019 | Copland | A61B 3/1173 351/206 |
| 2019/0232078 | A1 * | 8/2019 | Tai | A61B 3/12 |

* cited by examiner

*Primary Examiner* — Mahidere S Sahle
(74) *Attorney, Agent, or Firm* — Shay Glenn LLP

(57) ABSTRACT

A system for identifying structures in an eye of a subject. In embodiments of the invention, the system has a housing; a visible light source supported by the housing; an infrared light source supported by the housing; a photodetector supported by the housing; a patient interface disposed on an outer surface of the housing arranged and configured so that, when the patient interface is placed in contact with the subject, the subject's eye is aligned with the light sources and the photodetector such that the light sources illuminate an iris of the eye at an angle between 15° and 30° and such that the photodetector receives light from the light sources reflected by the iris; and a controller configured to activate the visible light source and the infrared light source and to obtain image information from the photodetector.

10 Claims, 4 Drawing Sheets

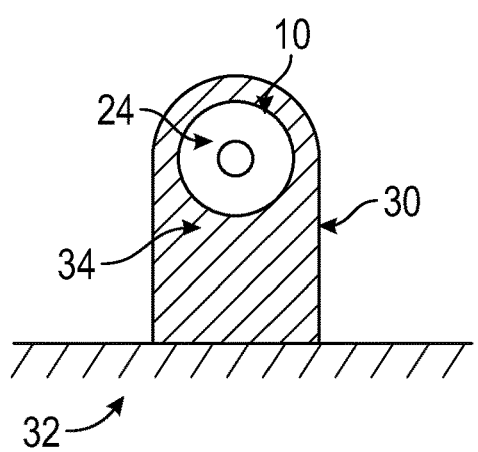
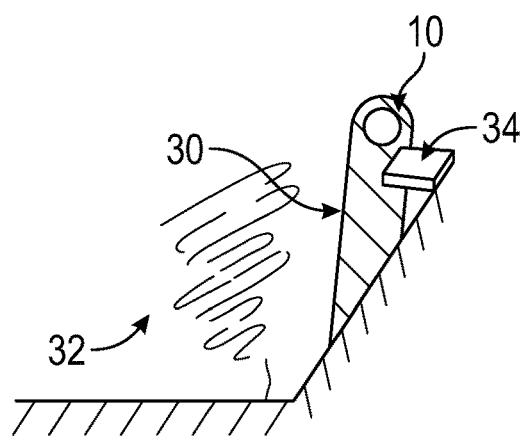
FIG. 7  FIG. 8
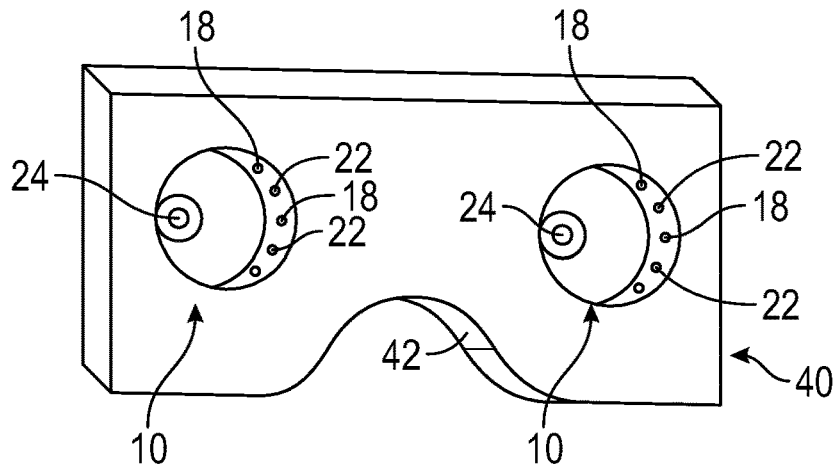
FIG. 9
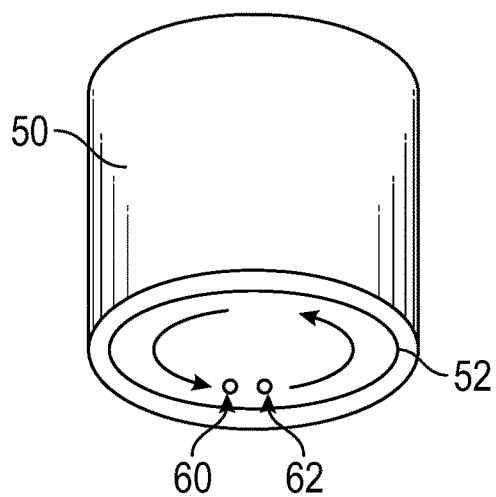
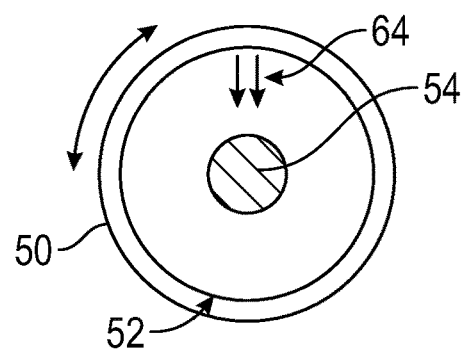
FIG. 10  FIG. 11

SYSTEM AND METHOD FOR DETECTION OF OCULAR STRUCTURES

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Neurofibromatosis is a genetic disorder that causes tumors to form on nerve tissue. One symptom of neurofibromatosis type 1 (NF1) is the presence of Lisch nodules (also known as iris hamartomas), which are small nodules on the iris of the subject's eye. These dome-shaped gelatinous masses are typically yellow-brown in color, and they project from the surface of the iris. Lisch nodules are currently detected by visual examination by a clinician using, e.g., a slit lamp. Qualitative evaluation of the size and number of Lisch nodules from such visual examination can provide information about the severity and progress of NF1 in the subject. It is also important to distinguish a suspected Lisch nodule from other structures that may be found in or on the iris, such as iris mammillations or iris nevi.

SUMMARY OF THE DISCLOSURE

The present invention relates to devices and methods for automating all or part of the identification, tracking and documentation of Lisch nodules. This invention may be useful in the diagnosis of neurofibromatosis as well as the assessment of treatment efficacy and disease progression.

One aspect of the invention provides a system for identifying structures in an eye of a subject. In embodiments of the invention, the system has a housing; a visible light source supported by the housing; an infrared light source supported by the housing; a photodetector supported by the housing; a patient interface disposed on an outer surface of the housing arranged and configured so that, when the patient interface is placed in contact with the subject, the subject's eye is aligned with the light sources and the photodetector such that the light sources illuminate an iris of the eye at an angle between 15° and 30° and such that the photodetector receives light from the light sources reflected by the iris; and a controller configured to activate the visible light source and the infrared light source and to obtain image information from the photodetector.

In some embodiments, the visible light source has a plurality of visible light emitters disposed in the housing at circumferentially spaced locations, each visible light emitter being configured to illuminate the iris at an angle between 15° and 30° when the patient interface is placed in contact with the subject. Likewise, in some embodiments, the infrared light source has a plurality of infrared light emitters disposed in the housing at circumferentially spaced locations, each infrared light emitter being configured to illuminate the iris at an angle between 15° and 30° when the patient interface is placed in contact with the subject. The photodetector may optionally be disposed in the housing radially inward and proximal to the light sources.

In some embodiments, the patient interface includes a compressible seal disposed on an edge of the housing distal to, and radially outside of, the light sources and the photodetector. The patient interface may also include a chin support adapted to support a chin of the subject. Alternatively, the patient interface may include a nose rest adapted to rest on a nose of the subject. In such embodiments, the system is adapted to engage with two eyes, and it includes a second visible light source supported by the housing and a second infrared light source supported by the housing, the first visible light source and the first infrared light source being arranged and configured to illuminate the iris of the first eye when the nose rest engages the subject's nose and the second visible light source and the second infrared light source being arranged and configured to illuminate an iris of a second eye of the subject when the nose rest engages subject's nose.

In some embodiments, the housing includes an inner light support rotatable within a stationary outer housing, and the visible and infrared light sources are supported by the inner light support.

Some embodiments of the invention include a transmitter operably connected to the controller to transmit image information to an external receiver.

Another aspect of the invention provides a method of obtaining Lisch nodule information from an eye of a subject. In embodiments of the invention, the method includes the steps of illuminating an iris of the eye with visible light at an angle between 15° and 30°; obtaining a reflection of the visible light with a photodetector; illuminating the iris with infrared light at an angle between 15° and 30°; obtaining a reflection of the infrared light; and identifying a Lisch nodule from the reflection of the visible light and the reflection of the infrared light.

In some embodiments, the method repeats the step of illuminating the iris with visible light from a plurality of positions around a circumference of the eye, obtaining a reflection of the visible light at each position, and the step of identifying a Lisch nodule includes the step of identifying a Lisch nodule from the reflection of infrared light and the reflections of visible light at each position. Likewise, some embodiments of the invention repeat the step of illuminating the iris with infrared light from a plurality of positions around a circumference of the eye, obtaining a reflection of the infrared light from each position, and the step of identifying a Lisch nodule includes the step of identifying a Lisch nodule from the reflection of visible light and the reflections of infrared light at each position.

Some embodiments of the invention include the step of placing a housing against a face of the subject at least partially surrounding the eye. In such embodiments the step of illuminating the iris with visible light includes the step of operating a visible light source disposed in the housing, the step of illuminating the iris with infrared light includes the step of operating an infrared light source disposed in the housing, and the steps of obtaining the reflection of the visible light and the reflection of the infrared light include the step of receiving the reflection of the visible light and the reflection of the infrared light with a photodetector disposed in the housing. In some such embodiments, a plurality of visible light sources are disposed in the housing at circumferentially spaced locations, and the method further includes the steps of serially illuminating the iris with each visible light source and obtaining a reflection of the visible light from each visible light source with the photodetector. In other such embodiments, the method includes the steps of moving the visible light source within the housing to a plurality of circumferential positions around the eye, illuminating the iris with visible light at each position, and obtaining a reflection of the visible light at each position, and the step of identifying a Lisch nodule includes the step of identifying a Lisch nodule from the reflection of infrared light and the reflections of visible light at each position. The method may also include the steps of moving the infrared light source within the housing to a plurality of circumferential positions around the eye, illuminating the iris with infrared light at each position, and obtaining a reflection of the infrared light at each position, and the step of identifying a Lisch nodule may include the step of identifying a Lisch nodule from the reflection of visible light and the reflections of infrared light at each position.

In embodiments of the method employing a housing, the housing may also include a light seal, and the method may also include the step of placing the light seal around the subject's eye to block ambient light from the subject's eye. The housing may also include a chin rest, and the step of placing the housing against the face may include the step of placing the subject's chin in the chin rest. The housing may also include a nose rest, and the step of placing the housing against the face may also include the step of placing the nose rest on the subject's nose.

In some embodiments, the step of identifying a Lisch nodule includes the step of identifying a shape of a projection from the iris. This step may also include the step of identifying a color of the projection.

Some embodiments of the invention also include a step of computing a volume and/or opacity of the Lisch nodule.

Some embodiments of the invention include the step of a map showing a location of a Lisch nodule on the subject's iris, a translation of a Lisch nodule on the subject's iris, a volumetric progression of a Lisch nodule on the subject's iris, and/or a merging of multiple Lisch nodules on the subject's iris.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 7 shows a front view of another embodiment of the invention.

FIG. 8 shows a perspective view of the embodiment of FIG. 7.

FIG. 9 shows a front view of yet another embodiment of the invention.

FIG. 10 shows a perspective view of still another embodiment of the invention.

FIG. 11 shows a bottom view of the embodiment of FIG. 10.

DETAILED DESCRIPTION

Figure 1:
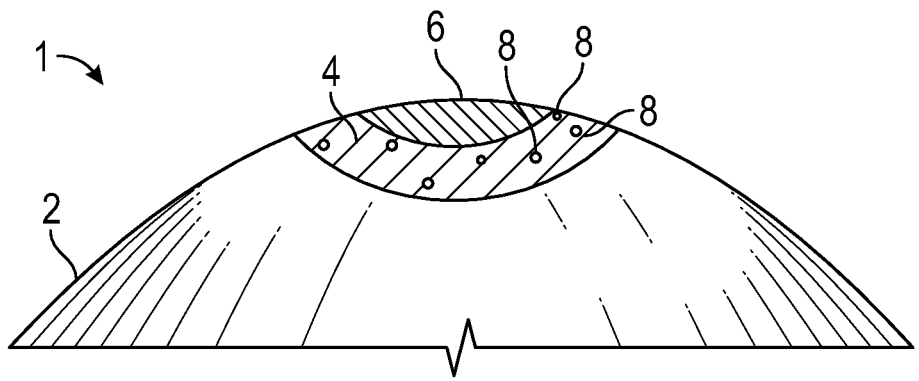
FIG. 1 is a stylized side view of an eye.

FIG. 1 is a stylized representation of a human eye 1 showing the sclera 2, the iris 4 and a dilated pupil 6. Dispersed in the retina 4 are multiple Lisch nodules 8. The invention described herein provides an automated and more accurate manner of identifying and quantifying Lisch nodules in a subject's eye.

FIGS. 2-6 show one embodiment of the invention. The imaging device 10 has a housing 12 that is placed against the face 14 of the subject surrounding an eye 1. A seal 16 provides an interface to provide proper positioning of the device and, in some embodiments, to block ambient light. Seal 16 may be, e.g., a compressible silicone pad.

Figure 2:
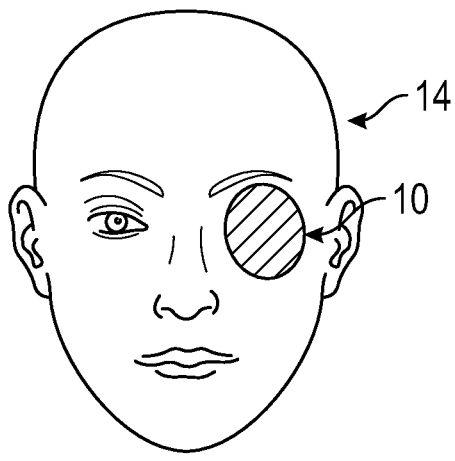
FIG. 2 shows an embodiment of the invention engaged with a subject's face.
Figure 3:
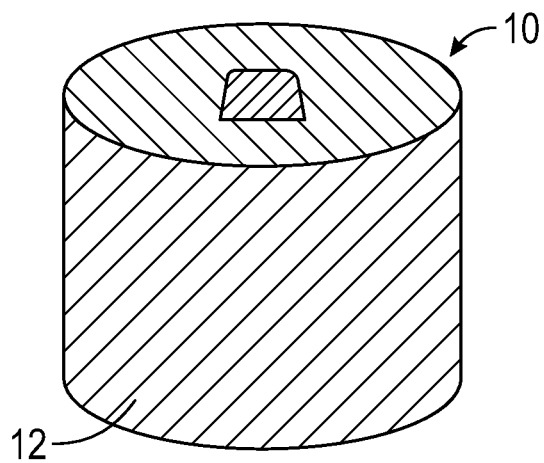
FIG. 3 shows a side elevational view of the embodiment of FIG. 2.
Figure 4:
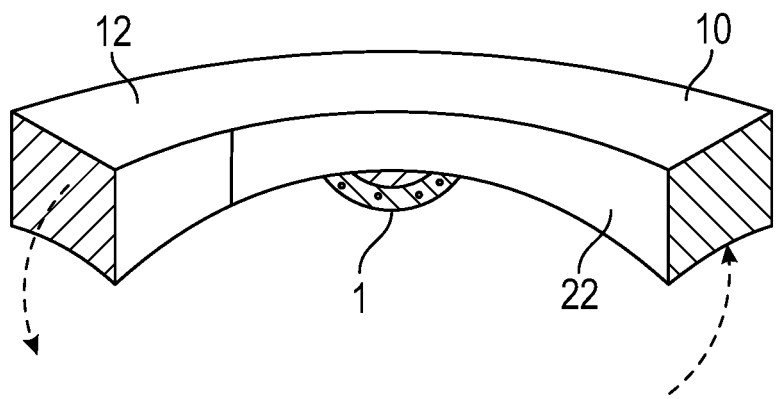
FIG. 4 shows a partial cross-section of the embodiment of FIGS. 2 and 3 over an eye of a subject.
Figure 5:
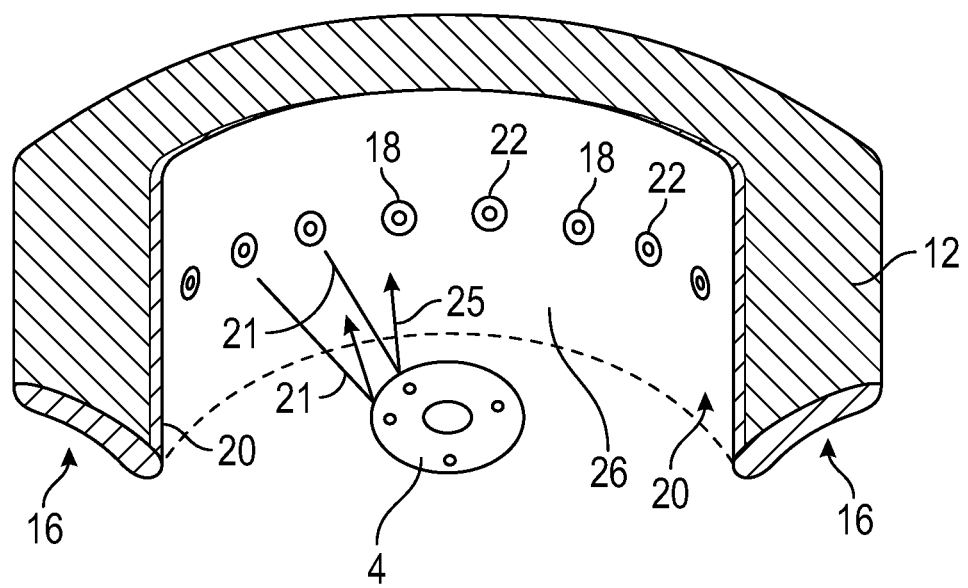
FIG. 5 shows another partial cross-section of the embodiment of FIGS. 2-4 over an eye of a subject.

Once in place surrounding eye 1, device 10 can illuminate the iris 4 with visible and infrared light from visible and infrared light sources supported by housing 12. In this embodiment, the visible light source is a plurality of visible light emitters 18 (e.g., LEDs) disposed around a circumference of an inner surface 20 of housing 12, and the infrared light source is a plurality of infrared light emitters 22 (e.g., LEDs) alternating with the visible light emitters 18 around the circumference of inner surface 20. In some embodiments, inner surface 20 is made from a non-reflective material or has a non-reflective coating. When the device 10 is in place around the subject's eye, as shown in FIGS. 2, 4 and 5, a controller (not shown) operates visible light emitters 18 and infrared light emitters 22 are arranged to illuminate the iris 4 at an angle of 15° to 30° from the plane of the iris, as shown by arrows 21 in FIG. 5. These shallow illumination angles create shadows in the reflected light that can provide volumetric information about nodules in the iris, as explained below.

Figure 6:
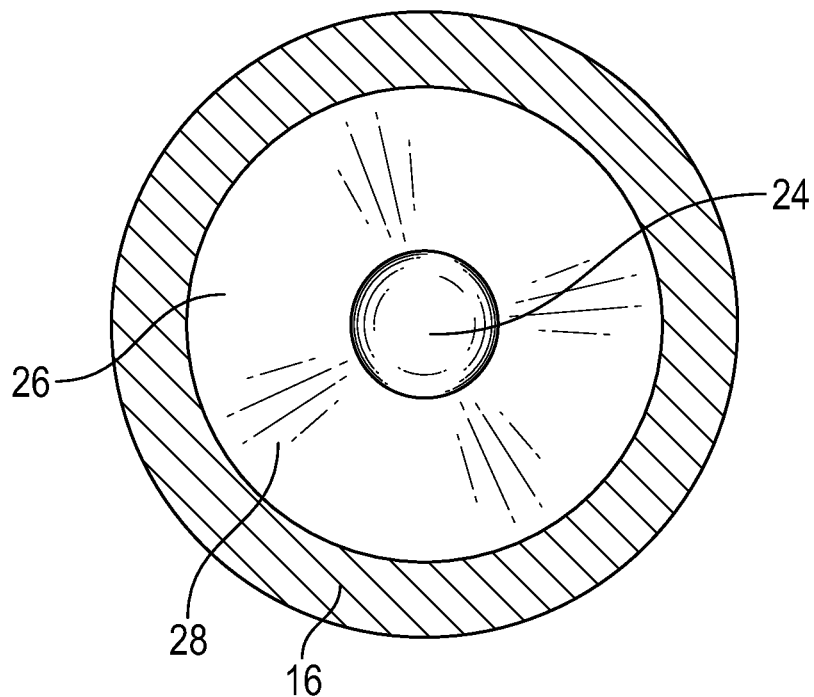
FIG. 6 shows a bottom elevational view of the embodiment of FIGS. 2-5.

A photodetector 24 (such as, e.g., a camera) faces downward toward the chamber 26 defined by inner surface 20 and the eye when the device is in place around the eye. Photodetector 24 receives light from the visible and infrared light sources reflected off of the iris, as shown by arrows 25 in FIG. 5. In one operation mode, each visible and infrared light emitter is fired individually in sequence to illuminate the iris until all light sources have been operated. In another mode, pairs or groups of light emitters may be activated together. Image data from photodetector 24 can then be stored in internal memory (not shown) or sent via a transmitter (such as, e.g., a WiFi transmitter, Bluetooth transmitter, etc., not shown) to an outside image processor (not shown). The image processor may consist of any analytical tooling (software or hardware) that can extract attributes such as, e.g., volume, color, shape, spatial orientation, and change in position of observed nodules. The image processor may use the visible-spectrum and infrared-spectrum image data to identify said attributes by, but not limited to, analyzing the appearance of the nodule in one image, analyzing the shadow cast by the nodule in one image, and analyzing a combination of images to render the desired results. The controller, internal memory, transmitter and energy source are disposed within housing 12. A transparent covering or lens 28 may cover the bottom of the photodetector, as shown in FIG. 6. In an optional embodiment (not shown), the open end of chamber 26 may be enclosed with a transparent covering or lens.

FIGS. 7 and 8 show another embodiment of the invention. In this embodiment, the device's housing 30 rests on a surface 32, such as a table. A device 10, such as described above, is supported by housing 30. Extending from the housing 30 is an adjustable chin rest 34 designed to align device 10 with the subject's eye when the subject's chin is resting on the chin rest. The controller, internal memory, transmitter and energy source are disposed within housing 30. A transparent covering may cover the subject side of the device, enclosing the chamber in which the photodetector 24 and light sources 18 and 22 are disposed.

FIG. 9 shows another embodiment of the invention. In this embodiment, two devices 10 are disposed within a goggle-shaped housing 40. Housing 40 has a nose rest 42 that aligns the devices 10 with the subject's eyes when nose rest 42 is placed against the top of the subject's nose. The controller, internal memory, transmitter and energy source are disposed within housing 40. Transparent coverings may cover the subject side of the device, enclosing the chambers in which the photodetectors 24 and light sources 18 and 22 are disposed.

FIGS. 10 and 11 show yet another embodiment of the device. The outer housing 50 of this embodiment is shaped like the embodiment of FIGS. 2-6 with an optional seal 52 serving as a patient interface. A photodetector 54 is at the top of an interior chamber 56, as in the earlier embodiments. Supported by the outer housing 50 is a rotatable inner housing 58 supporting a visible light source 60 and an infrared light source 62, both of which are arranged a to illuminate an iris of an eye surrounded by seal 52 at an angle of 15° to 30° from the plane of the iris, as shown by arrows 64. Inner housing 58 may be rotated manually or with a motor (not shown) to illuminate different sides of the subject's iris. This embodiment uses fewer light sources than the embodiment of FIGS. 2-6 while obtaining the same results. Other embodiments may use any number of light sources to obtain the images. Photodetector 54 receives light from the visible and infrared light sources reflected off of the iris, as in the earlier embodiments. Image data from photodetector 54 can then be stored in internal memory (not shown) or sent via a transmitter (not shown) to an outside image processor (not shown). The image processor may consist of any analytical tooling (software or hardware) that can extract attributes such as, e.g., volume, color, shape, spatial orientation, and change in position of observed nodules. As in the earlier embodiment, the image processor may use the visible-spectrum and infrared-spectrum image data to identify said attributes by, but not limited to, analyzing the appearance of the nodule in one image, analyzing the shadow cast by the nodule in one image, and analyzing a combination of images to render the desired results.

Figure 12:
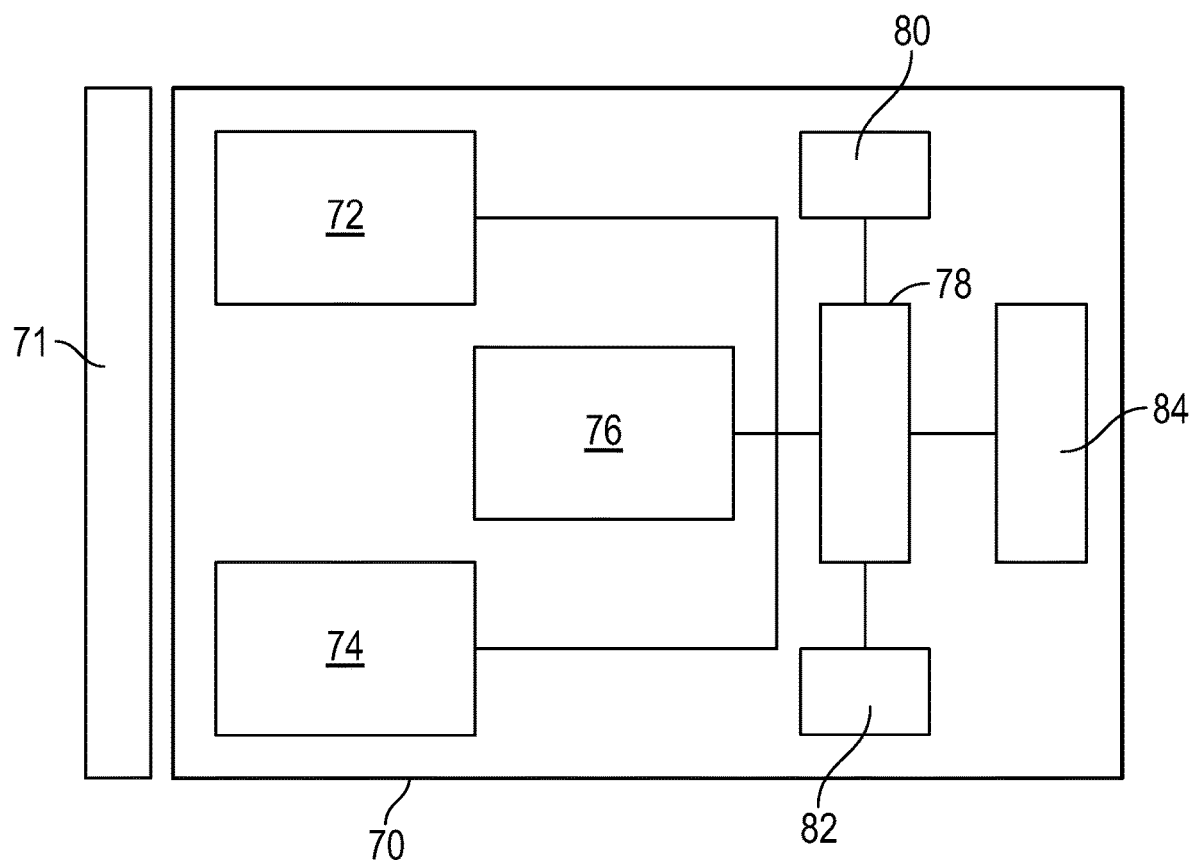
FIG. 12 shows a block diagram of a system according to an embodiment of the invention.

FIG. 12 is a block diagram showing some features that may be common to all embodiments of the invention. Supported by housing 70 are a patient interface 71, a visible light source 72, an infrared light source 74, a photodetector 76, a controller 78, a transmitter 80, memory 82, and a power source 84. When patient interface 71 is placed against the subject, controller 78 operates light sources 72 and 74, which are arranged to illuminate an iris of the subject's eye at an angle of 15° to 30° from the plane of the iris. Photodetector 76 receives light from the visible and infrared light sources reflected off of the iris, as in the earlier embodiments. Under control of controller 78, image data from photodetector 76 can then be stored in internal memory 82 or sent via transmitter 80 to an outside image processor (not shown). Power source 84 provides power to the system. The image processor may consist of any analytical tooling (software or hardware) that can extract attributes such as, e.g., volume, color, shape, spatial orientation, and change in position of observed nodules. As in the other embodiments, the image processor may use the visible-spectrum and infrared-spectrum image data to identify said attributes by, but not limited to, analyzing the appearance of the nodule in one image, analyzing the shadow cast by the nodule in one image, and analyzing a combination of images to render the desired results.

References to "analytical tooling," "analysis," and "image/data processing" herein pertain to methods of identifying a Lisch nodule including the combined software analysis of the color, shape and opacity of a potential nodule in order to classify it as a Lisch nodule. Because Lisch nodules present with distinct geometry and color compared to surrounding tissue, such attributes can be used to discriminate between Lisch nodules and other tissue types and can describe specific attributes of a nodule that may be useful in patient diagnosis and treatment. In some embodiments, pairs of visible and infrared emitters are fired in echelon and in tandem, and reflections of that light from the subject's iris are captured with a photosensor until all desired lighting angles have been recorded. This approach captures images in both visible and infrared spectra portraying the iris under multiple lighting angles, and the differing lighting angles will cause shadows of differing directions to be cast by the projections on the iris. Then, using existing image segmentation techniques, all visible projections on the iris in the visual and infrared image collections are segmented into isolated images of said projections for later processing steps, and each isolated image is coupled with a 2-dimensional coordinate for locating said isolated image on the subject's iris. Each isolated image may also be coupled with information identifying the eye from which the image was captured. Because the collections of visible and infrared isolated/segmented images will contain replicate nodules from different captures on the same eye but of different lighting configurations, multiple image collections will be formed, each containing isolated visual and infrared images of one nodule grouped by their corresponding coordinates.

At this point, each visible nodule on the iris will have an associated collection of both visible and infrared isolated images portraying the nodule under different lighting configurations. The image data contained in each said collection can provide color, opacity, 2-dimensional shape, 3-dimensional shape, 2-dimensional size, 3-dimensional size (volume), and 2-dimensional location on the iris for the associated nodule. For example, the volume of a Lisch nodule can be determined through combined analysis of multiple visible and IR images such that the comparison of the shadows contained therein reveals the geometric and volumetric attributes of the nodule. The opacity of a Lisch nodule can be determined by analyzing the difference between the infrared and visible images taken from one configuration of emitters and specifically examining the difference in light penetration in the nodule. The color of the nodule is determined through existing color analysis techniques applied to the segmented visible spectrum image of the nodule. Opacity of the nodule is determined by comparing the visual light and infrared light images for each capture angle and analyzing the difference in light penetration of the tissue between the images; a comparison of the edges of the nodule in the infrared images to the edges of the nodule in the visible images will show differences in light penetration and, thus, the opacity of the tissue.

The 2-dimensional shape and size of the nodule are determined through existing image segmentation and edge detection techniques applied to the visual and infrared isolated images of the nodule. The 3-dimensional shape and size of the nodule are determined by performing combined analysis on the infrared images for each nodule. The shadows cast at each capture angle of said nodule are processed using a computer algorithm in order to estimate the volume and 3-dimensional geometry of the Lisch nodule. By recording the shadows cast by a nodule at different lighting configurations, an algorithmic model can be built to accurately estimate the volume and 3-dimensional shape of the nodule by extracting the information encoded in the multitude of shadows for each nodule. Using the position of the nodule recorded at the step of isolating the nodular images, software may construct a map of the patient's iris visually demonstrating the locations of said nodules and projections using said 2-dimensional coordinates. All said methods combine to provide medical professionals with a novel tooling suite that both facilitates existing tasks, such as identifying Lisch nodules, and also provides novel or higher fidelity observations than those which are presently available. Attributes such as color, position, 2-dimensional shape, and 2-dimensional size would have higher fidelity than the features obtained using state-of-the-art approaches, while opacity, 3-dimensional shape, and nodular volume would provide novel, useful information to medical professionals. Additionally, the data collected using the device and methods of this invention can be organized to provide the medical professional with new ways of assessing disease progression and change. Novel attributes such as location, volumetric progression, merging of multiple nodules, 3-dimensional shape, volume, and opacity, along with higher fidelity 2-dimensional shape, 2-dimensional size, and position attributes may be tracked over time using multiple scans of the same patient in order to assess treatment efficacy and/or disease progression. The software suite of this invention can be combined with existing dermatological data from other documentary sites in order to jointly diagnose and track the disease (Neurofibromatosis) in any given subject with greater efficacy and insight.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for identifying a Lisch nodule in an eye of a subject, the system comprising:
    a housing having an interior chamber with an open end and a closed end;
    a visible light source supported by the housing adjacent the open end of the housing;
    an infrared light source supported by the housing adjacent the open end of the housing;
    a photodetector supported by the housing at the closed end of the housing;
    a patient interface disposed on an outer surface of the housing arranged and configured so that, when the patient interface is placed in contact with the subject, the subject's eye is aligned with the light sources and the photodetector such that the light sources illuminate an iris of the eye at an angle between 15° and 30° and such that the photodetector receives light from the light sources reflected by the iris, the patient interface comprising a compressible seal surrounding the open end of the housing distal to, and radially outside of, the light sources and the photodetector and adapted to be placed against the subject's face to block ambient light from the interior chamber; and
    a controller configured to activate each of the visible light source and the infrared light source to illuminate the iris with visible light and infrared light, respectively, from a plurality of circumferentially spaced locations and to obtain image information from the photodetector from light from the light sources reflected by the iris, the image information comprising a shadow cast by the Lisch nodule and the color and location of the Lisch nodule.

2. The system of claim 1 wherein the visible light source comprises a plurality of visible light emitters disposed in the housing at circumferentially spaced locations, each visible light emitter being configured to illuminate the iris at an angle between 15° and 30° when the patient interface is placed in contact with the subject.

3. The system of claim 1 wherein the infrared light source comprises a plurality of infrared light emitters disposed in the housing at circumferentially spaced locations, each infrared light emitter being configured to illuminate the iris at an angle between 15° and 30° when the patient interface is placed in contact with the subject.

4. The system of claim 1 wherein the housing comprises an inner light support rotatable within a stationary outer housing, the visible and infrared light sources being supported by the inner light support.

5. The system of claim 1 further comprising a transmitter operably connected to the controller to transmit image information to an external receiver.

6. A system for identifying a Lisch nodule in an eye of a subject, the system comprising:
    a housing having an interior surface surrounding an interior chamber with an open end and a closed end;
    a plurality of visible light sources supported by the housing on the interior surface;
    a plurality of infrared light sources supported by the housing on the interior surface;
    a photodetector supported by the housing and disposed to face toward the interior chamber and the open end of the housing;
    a patient interface disposed on an outer surface of the open end of the housing arranged and configured so that, when the patient interface is placed in contact with the subject, the subject's eye is aligned with the light sources and the photodetector such that the light sources illuminate an iris of the eye at an angle between 15° and 30° and such that the photodetector receives light from the light sources reflected by the iris; and
    a controller configured to activate the visible light source and the infrared light source and to obtain image information from the photodetector from light from the light sources reflected by the iris, the image information comprising color and location of the Lisch nodule.

7. The system of claim 6 wherein the plurality of visible light sources are disposed at circumferentially spaced locations and the plurality of infrared light sources are disposed at circumferentially spaced locations.

8. The system of claim 6 wherein the plurality of visible light sources and the plurality of infrared light sources are disposed adjacent the open end of the interior chamber.

9. The system of claim 6 wherein the photodetector is disposed in the housing radially inward and proximal to the light sources.

10. The system of claim 6 further comprising a transmitter operably connected to the controller to transmit image information to an external receiver.

* * * * *